United States Patent [19]
Phillips

[11] Patent Number: 5,487,314
[45] Date of Patent: Jan. 30, 1996

[54] WATER SAMPLING APPARATUS

[75] Inventor: William H. Phillips, Saginaw, Mich.

[73] Assignee: Trippensee Corporation, Saginaw, Mich.

[21] Appl. No.: 236,268

[22] Filed: May 2, 1994

[51] Int. Cl.⁶ ................................................ G01N 1/12
[52] U.S. Cl. ............................................... 73/864.66
[58] Field of Search ........................ 73/864.63, 863.71, 73/864.6, 864.67, 864.65

[56] References Cited

U.S. PATENT DOCUMENTS

| | | | |
|---|---|---|---|
| 2,071,145 | 2/1937 | Summers | 73/864.65 |
| 2,314,372 | 3/1943 | Spilhaus | 73/864.63 X |
| 3,379,065 | 4/1968 | Gibbon | 73/864.65 |
| 3,841,162 | 10/1974 | Duperon | 73/864.67 |
| 4,027,538 | 6/1977 | Snyder et al. | 73/864.67 |
| 4,580,454 | 4/1986 | Deja | 73/864.63 |
| 4,594,905 | 6/1986 | Roberts | 73/864.63 |

Primary Examiner—Thomas P. Noland
Attorney, Agent, or Firm—Learman & McCulloch

[57] ABSTRACT

A Kemmerer style water sampler has a tubular body open at both ends and through which a connecting rod extends. One end of the connecting rod is fixed to a lower closure and has a latch mechanism at its other end coupled to an upper closure. The latch mechanism is releasable by means of an actuator which is movable in response to the application thereon of a tensile force in a direction to release the latch and enable the closures to move to body sealing positions. The tensile force may be applied on the actuator in virtually any position of the tubular body.

11 Claims, 1 Drawing Sheet

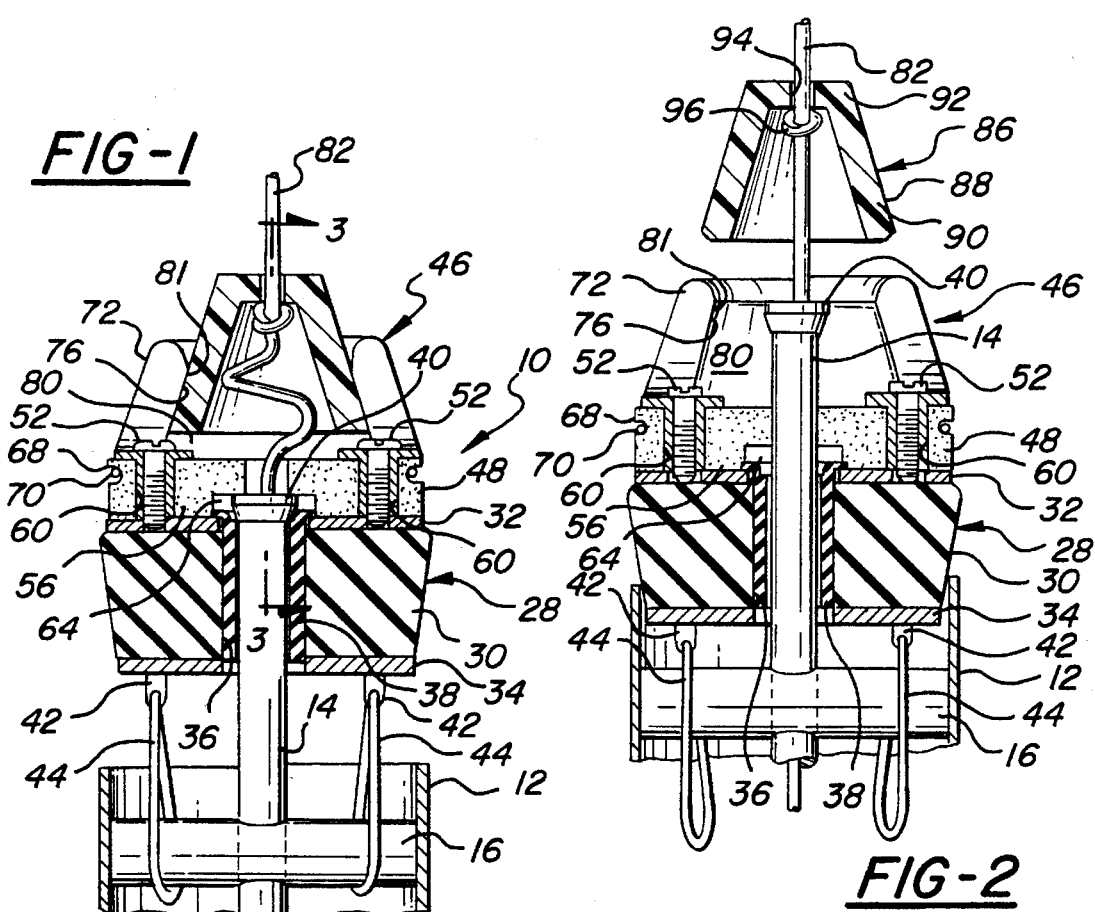
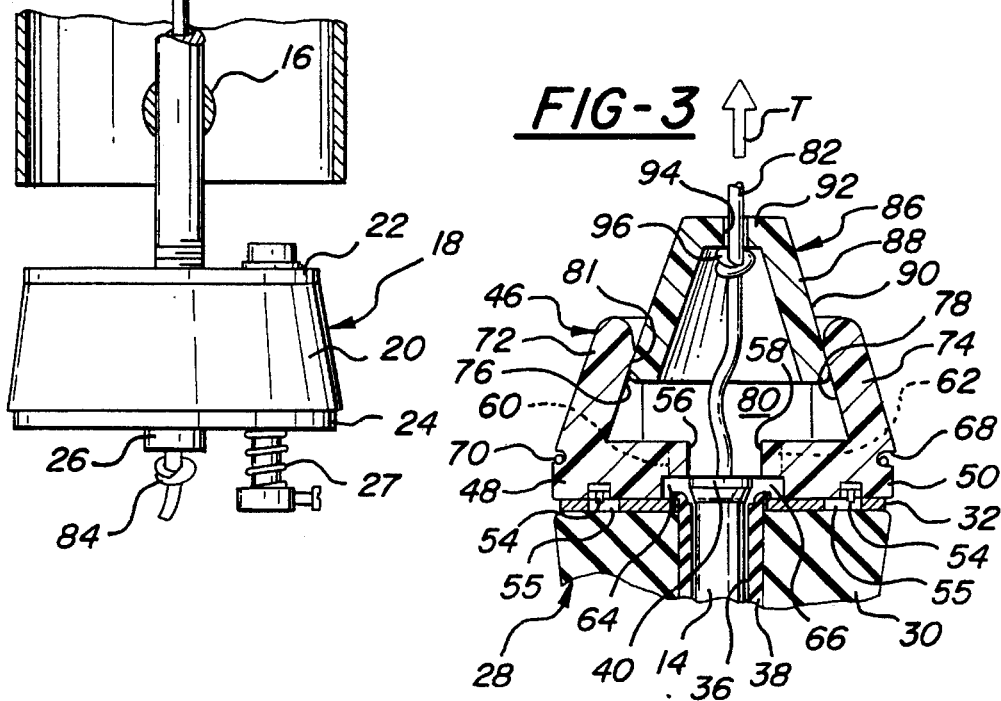

WATER SAMPLING APPARATUS

This invention relates to water sampling apparatus of the kind that is adapted to be lowered into a body of water to entrap in the tube a sample of water from a selected depth. Sampling devices of the kind to which the invention relates conventionally are known as Kemmerer style water samplers. Such a sampler is shown in U.S. Pat. No. 3,841,162.

BACKGROUND OF THE INVENTION

For some limnological and oceanographic studies it is important that samples of water at different depths be taken and that such samples be protected against dilution or modification due to leakage of the sampler during retrieval of the latter. The Kemmerer style water sampler was designed for this purpose and comprises a hollow tube, normally open at both ends, and having top and bottom closures or stoppers which are adapted to be moved from open positions to sealing positions in response to the dropping of a weighted messenger along the line or cable which supports the sampler. The stoppers of a Kemmerer style sampler are latched in their open positions and the upper stopper includes a latch release mechanism which is tripped by the weighted messenger to enable the stoppers to move to their closed positions. Such samplers, however, have their limitations, particularly when the sampler is to be used in a position where it and the line are inclined to the vertical because of currents or the like, as a result of which the weighted messenger may be unable to descend to the sampler or may be unable to strike the release mechanism with a force insufficient to trip the latch.

SUMMARY OF INVENTION AND ADVANTAGES

Water sampling apparatus according to the invention comprises a hollow body that is open at its opposite ends and having associated therewith a pair of closure members joined by connecting means which enable relative movements of the closure members toward and away from one another and toward and away from the associated ends of the body to effect sealing and unsealing of the ends of the body. A latch mechanism carried by the connecting means includes an enlargement for releasable engagement by a pair of clasp members mounted on one of the closure members to disable and enable, respectively, the relative movements of the coupling members. The latch mechanism includes a part forming a reentrant pocket in which an actuating plug releasably is accommodated. The plug is displaceable from the pocket in response to the application on the plug of a tensile force, thereby releasing the latch and enabling the closures to seal the opposite ends of the body.

The latch actuating mechanism obviates the need for a weighted messenger and is effective to release the latch regardless of the angle of the tether line to which the sampler is attached.

THE DRAWINGS

A presently preferred embodiment of the invention is disclosed in the accompanying drawing, wherein:

FIG. 1 is a fragmentary, elevational view, partly in section, of a Kemmerer style water sampler illustrating the latch mechanism in engaged condition and the closures of the sampler latched in their open positions;

FIG. 2 is a fragmentary sectional view similar to FIG. 1, but illustrating the latch mechanism in the tripped condition and the top closure of the sampler moved to the closed position; and FIG. 3 is a fragmentary sectional view taken on the line 3—3 of FIG. 1, but illustrating the latch mechanism in the latch disengaged condition.

DETAILED DESCRIPTION

Apparatus constructed according to a presently preferred embodiment of the invention is indicated generally at 10 in the drawings and comprises a water sampler of the Kemmerer type having a cylindrical, tubular sampler body 12 that is open at both ends. A hollow connecting rod 14 extends through the body 12 and is slideably supported by a pair of transverse guides 16 that are fixed to the interior of the body 12. The rod 14 has a considerably greater length than that of the body 12 and is fixed at its lower end to a lower closure member 18 comprising a truncated, conical stopper 20 formed of rubber or rubbery material sandwiched between metallic plates 22 and 24. The lower end of the rod 14 is threaded and extends through aligned threaded apertures of the plates 22 and 24 and is fixed with respect thereto by a locking collar 26 that is threaded onto the rod tightly against the bottom plate 24. An outlet 27 of conventional construction also is incorporated in the closure 18 for the purpose of permitting the contents of the body 12 to be drained when desired.

The sampler apparatus also includes an upper closure member 28 having a truncated, conical stopper 30 formed of rubbery or rubber material sandwiched between metal plates 32 and 34. The stopper and plate members are provided with an aligned bore 36 within which is located a sleeve 38 secured at its opposite ends to the plates 32 and 34, respectively. The sleeve 38 slideably accommodates the connecting rod 14.

The upper end of the connecting rod 14 is provided with an enlargement or latch part 40 having a greater dimension than that of the sleeve 38 and located above the upper end of the sleeve 38 of the upper closure member 28 so as to prevent movement of the closure 28 off the upper end of the rod 14. The upper closure member 28, however, is capable of sliding in the opposite direction along the rod toward the opposite or lower closure 18. Depending from the underside of the lower plate 34 are anchor lugs 42 from which are hung a pair of endless retaining cables 44, the lower ends of which are looped around the upper guide 16. The cables 44 limit movement of the upper closure member 28 in a direction away from the adjacent end of the body 12, but permit movement of the closure 28 toward the body so as to enable the closure to seat on and seal the adjacent or upper end of the body 12.

The apparatus thus far described is conventional in a Kemmerer style water sampler and forms no part of the invention per se, aside from the manner in which it cooperates with other components of the apparatus yet to be described.

A latch mechanism constructed according to the invention is designated generally by the reference character 46 and comprises a pair of segment-shaped clasp members or plates 48 and 50 mounted on the upper plate 32 for linear lateral reciprocating movements toward and away from one another. The clasp plates 48 and 50 are similar to the corresponding parts of the construction shown in the aforementioned patent and are mounted by means of headed screws 52 carried by the plate 32 in diametrically opposed positions, the heads of the screws projecting beyond the level of the clasp plates 48 and 50 so as to permit the latter to be accommodated between the plate 14 and the heads of the screws. Guide pins 54 (FIG. 3) project from the bottom of the clasp plates and are accommodated in radial slots 55 of the top plate 32 to guide the clasp plates linearly toward and away from one another.

The clasp plates 48 and 50 have confronting edges 56 and 58, respectively, which are adapted to abut one another. To enable the edges to abut one another, they are provided with semi-circular recesses 60 and 62 at their opposite ends for the accommodation of the shanks of the screws 52 and 54. The confronting surfaces 56 and 58 of the clasp plates also are recessed as at 64 and 66, so as to provide an opening of such size as to accommodate the enlargement 40 on the rod 14 when the confronting edges 56 and 58 abut one another.

The clasp plates 48 and 50 are formed with an annular encircling groove 68 in which an undersized endless spring 70 is accommodated for constantly urging the clasp plates 48 and 50 toward one another.

A pair of laterally opposed ears or lugs 72 and 74 are fixed at their lower ends to the clasp plates 48 and 50, respectively, and extend upwardly therefrom to opposite free ends. Movement imparted to the ears 72 and 74 effects corresponding movement of the associated clasp plates 48 and 50. The ears 72 and 74 have inner wall surfaces 76 and 78, respectively, that converge upwardly toward one another and form a reentrant, frustoconical pocket 80 between the ears having a restricted opening 81 at its upper or free end.

One end of a combined tether and release line or cable 82 extends through the hollow connecting rod and is provided at its lower end with a knot 84 or other enlargement below the lower enclosure plate 24 to prevent return movement of the line through the rod, thereby enabling the line 82 to support the entire sampling apparatus. The line 82 extends through a frustoconical latch actuator 86 above the upper end of the connecting rod 14. The actuator 86 comprises a hollow body or plug 88 having a side wall 90 that is tapered to correspond to the taper of the inner walls 76 and 78 of the ears 72, 74. The plug is releasably captured within the reentrant pocket 80 when the clasp plates 48 and 50 are engaged with the latch 40 (see FIG. 1). The plug 88 is open at its lower end and tapers upwardly to an end wall 92 at its upper end having an aperture 94 therein through which the release line 82 extends. The line 82 is coupled to the plug 88 via a knot 96 or other enlargement accommodated within the plug 88 which is of such size as to be incapable of passing through the aperture 94. As also illustrated in FIG. 1, the line 82 is slack between the upper and lower enlargements 96 and 84. The slack is such as to enable the plug 88 to be withdrawn from the pocket 80 via the line 82.

To condition the apparatus for operation, the latch part 40 at the upper end of the rod 14 is fitted into the recesses 64 and 66 between the plates 48 and 50 and the actuator plug 88 fitted into the pocket 80 as shown in FIG. 1 to provide support for the upper closure member 28.

When the closure 28 is supported by the latch part 40, the entire sampling apparatus may be suspended from the line 82 via the engagement of the enlargement 96 with the inner surface of the end wall 92 of the release plug 88. The weight of the apparatus is insufficient to dislodge the plug 88 from the pocket 80. The body 12 is supported by means of the retaining cables 44 at a fixed distance below the upper closure 28, and the lower closure 18 is supported by the connecting rod 14 at a fixed distance below the lower end of the body 12. In these relative positions of the parts, both ends of the sampler body 12 are open and the sampling apparatus may be lowered to any submerged depth in a body of water.

When the sampler has been lowered to a desired depth, the body 12 may be closed by pulling on the line 82 in the direction of arrow T (FIG. 3) to apply a sharp tensile force to the actuator plug 88 for the purpose of pulling the plug 88 out of the pocket 80, as illustrated in FIG. 2. The plug 88 is of such relative size with respect to the pocket that, as the plug passes out of the pocket, it causes the ears 72 and 74 and hence the clasp plates 48 and 50 to move away from one another against the force of the spring 70, thereby enlarging the opening defined by the recesses 64 and 66, as illustrated in FIG. 3. When the diameter of such opening is equal to or greater than that of the latch part 40, the weight of the upper closure 28 will cause the latter to fall toward the upper end of the sampling body 12. As the closure 28 falls, the body 12 also will fall toward the closure 18 until such time as the latter seats in the lower end of the body 12. Following seating of the closure 18, the closure 28 will seat in the upper end of the body (FIG. 2), thereby sealing both ends of the sampler body 12. The sampler apparatus then may be hoisted by means of the line 82.

A particularly advantageous characteristic of the invention is that the line 82 need not be vertical to enable withdrawal of the actuator plug 88 and sealing of both ends of the sampler. Consequently, the sampler may be cast at an angle into a body of water from a pier, the bank of a stream, or from a boat. Furthermore, the sampler may be used in bodies of water having strong currents which act on the body to cause the line 82 to assume a position inclined to the vertical.

The disclosed embodiment is representative of the preferred form of the invention, but is intended to be illustrative rather than definitive thereof. The invention is defined in the claims.

I claim:

1. Water sampling apparatus comprising:

a hollow body open at its opposite ends and adapted to be lowered to a predetermined depth in a body of water;

a first closure member for one end of said body;

a second closure member for the other end of said body;

a connecting rod connecting said first and said second closure members for relative movements toward and away from one another and toward and away from sealing relation with the associated ends of said body;

a latch carried by said connecting rod;

a pair of clasp members mounted on one of said closure members and movable laterally of one another into and out of engagement with said latch for disabling and enabling said relative movements of said closure members;

a pair of laterally opposed ears carried by said clasp members and extending therefrom to form a reentrant pocket between said ears; and a release line having a plug releasably captured within said pocket and of such relative size as to move said ears and said clasp members away from one another by an amount sufficient to effect disengagement of said latch by said clasp members in response to the application of a force on said line sufficient to withdraw said plug from said pocket, whereby said closure members are enabled to effect closure of said hollow body.

2. The apparatus of claim 1 wherein said plug is coupled to said release line adjacent one end of said connecting rod.

3. The apparatus of claim 2 wherein said pocket is tapered toward a restricted opening.

4. The apparatus of claim 3 wherein said plug is tapered complementally to said pocket.

5. The apparatus of claim 4 wherein each of said pocket and said plug is frustoconical.

6. The apparatus of claim 2 wherein said plug has an aperture through which said release line extends, said release line having a first enlargement between said plug and said one end of said connecting rod, said enlargement being of such size as to be incapable of passing through said aperture.

7. The apparatus of claim 6 wherein said release line extends from said enlargement through aligned openings in said connecting rod and the other of said closure members to a free end, said free end having a second enlargement spaced from said first enlargement and being of such size as to be incapable of passing through said opening of said other closure member.

8. The apparatus of claim 7 wherein said connecting rod has a fixed length and said spacing between said enlargements is greater than said length of said connecting rod.

9. Water sampling apparatus comprising:
- a hollow tubular body open at its opposite ends and adapted to be lowered to a submerged position in a body of water;
- a first closure member for one end of said body;
- a second closure member for the opposite end of said body;
- a connecting rod extending through said body and fixed at one end to said second closure member and supporting said first closure member for relative movements toward and away from said second closure member to effect closing and opening of said ends of said body;
- a latch carried by the upper end of said connecting rod;
- a pair of clasp members mounted on said upper closure member and movable laterally toward and away from one another into and out of engagement with said latch for disabling and enabling said relative movements of said coupling members;
- a spring constantly urging said clasp members toward one another;
- a pair of laterally opposed ears fixed to said clasp members defining a reentrant pocket therebetween;
- an actuating plug releasably captured within said pocket;
- a release line extending through said release plug, said clasp members, said upper closure member, said connecting rod, and said lower closure member and terminating in a free end;
- a lower stop secured to said line adjacent said free end; and
- an upper stop secured to said line between said plug and said upper closure member, said upper stop confronting said plug, said plug being of such size relative to said pocket that as said plug moves out of said pocket it displaces said ears and thereby said clasp members away from one another by an amount sufficient to effect disengagement of said latch by said clasp members in response to the application of a force to said line sufficient to withdraw said plug from said pocket, whereby said closure members are enabled to effect closure of said body.

10. Water sampling apparatus comprising a hollow tubular body open at its opposite ends and adapted to be lowered to a submerged position in a body of water; a first closure member for one end of said body; a second closure member for the opposite end of said body; a connecting rod fixed to said second closure member and extending through said body and said first closure member; latch means reacting between said connecting rod and said first closure member for releasably coupling said first closure member in a fixed position on said connecting rod in which both of said closure members are spaced from the respective ends of said body so as to maintain said body open at both of its ends; latch operating means for releasing said latch means; and combined tether and actuating means coupled at least indirectly to said tubular body for suspending the latter at a selected depth and also coupled to said latch operating means, said combined tether and actuating means being operable in response to the application of force thereon in a direction away from said body to release said latch means and enable said closure members to seal the opposite ends of said body.

11. The apparatus of claim 10 wherein said force may be applied to said actuating means regardless of the position of said body in said body of water.

* * * * *